United States Patent [19]

Burkholder

[11] B 4,001,338

[45] Jan. 4, 1977

[54] PURIFICATION OF DIALKYLBENZENE DIHYDROPEROXIDE

[75] Inventor: Ward J. Burkholder, Houston, Tex.

[73] Assignee: The Goodyear Tire & Rubber Co., Akron, Ohio

[22] Filed: July 25, 1969

[21] Appl. No.: 845,044

[44] Published under the second Trial Voluntary Protest Program on March 30, 1976 as document No. B 845,044.

[52] U.S. Cl. ........................ 260/610 A; 260/610 B; 203/14

[51] Int. Cl.² ........................................ C07C 179/02

[58] Field of Search .................. 260/610 A, 610 B; 203/14, 69

[56] References Cited

UNITED STATES PATENTS

| | | | |
|---|---|---|---|
| 2,715,646 | 12/1959 | Hawkins et al. | 260/610 B |
| 2,915,557 | 8/1955 | Kreps et al. | 260/610 A |
| 3,190,923 | 6/1965 | Sodomann et al. | 260/610 |

*Primary Examiner*—Bernard Helfin
*Assistant Examiner*—W. B. Lane

[57] ABSTRACT

An improved method for separating para-dialkylbenzene monohydroperoxide from crude solid para-dialkylbenzene dihydroperoxide which comprises treating the solid dihydroperoxide with a liquid hydrocarbon to form a mixture, heating the mixture to a temperature of at least about 60° C., cooling the mixture to below about 30° C. and filtering or otherwise physically separating the solid dihydroperoxide.

2 Claims, No Drawings

PURIFICATION OF DIALKYLBENZENE DIHYDROPEROXIDE

BACKGROUND OF THE INVENTION

The oxidation of alkyl substituted aromatic hydrocarbons and particularly dialkyl aromatics under suitable conditions to yield the corresponding dihydroperoxides is well known. The aromatic dihydroperoxides have found use as oxidizing agents and free radical initiators for a number of polymerization processes and are valuable in preparing polyhydric phenols such as hydroquinone, resorcinol and the like. In preparing the latter products, it is well known to rearrange the dihydroperoxide percursors in the presence of acid catalyst to form the corresponding phenol and carbonyl compound.

A most efficient means for preparing dihydroperoxides such as para-diisopropylbenzene dihydroperoxide includes an oxidation reaction in which para-dialkylbenzene is oxidized in the presence of an alkaline material. In preparing the dihydroperoxides it is also the practice to continue the reaction only partially to completion, based on the total amount of dialkylbenzene present. It is found that at higher concentrations the dihydroperoxide begins to decompose resulting in a reduced yield of dihydroperoxide based upon dialkylbenzene feed. Yet, since the reaction is carried only to partial completion, large amounts of monohydroperoxide, the dihydroperoxide intermediate, as well as unreacted dialkylbenzene are present in the oxidation reaction mixture. Thereafter, as the solid dihydroperoxide product is recovered by suitable techniques, significant amounts of these precursors are retained in the solid product. Accordingly, it is desirable to separate the monohydroperoxide and dialkylbenzene from the dihydroperoxide to achieve improved quality of the latter product as well as to recover the valuable precursors for recycle to the oxidation reaction.

A number of techniques have been proposed for recovering solid dihydroperoxide free from monohydroperoxide. A common method for separating dihydroperoxides from monohydroperoxides has been to subject mixtures of these products to an aqueous alkaline solution, usually dilute sodium hydroxide, to form the sodium salts of the two hydroperoxides. The salt of the monohydroperoxide remains in the organic phase, while the salt of the dihydroperoxide dissolves in the aqueous phase. The aqueous phase is separated from the organic phase, neutralized with a weak acid and the dihydroperoxide precipitates and is recovered. One objection to such a separation technique is that additional water is added to the dihydroperoxide which must be subsequently removed. The presence of moisture is especially undesirable where the dihydroperoxide is to be rearranged as previously noted since it dilutes the acid catalyst and lowers reaction rates. Further, separation of the organic and aqueous phases and neutralization require acid consumption and additional process steps in order to recover uncontaminated dihydroperoxide in good yield.

Another method proposed for separating dialkylbenzene and monohydroperoxide from solid dihydroperoxide comprises repeatedly washing or resuspending the product with a suitable solvent and filtering the dihydroperoxide until the desired purity is achieved. It will be appreciated that such repeated washing or suspension and refiltering of the hydroperoxide product mixture with additional amounts of hydrocarbon would eventually result in successful sufficient separation of the products. However, concomitantly, the technique also results in the loss of unnecessary amounts of dihydroperoxide even by use of a hydrocarbon such as benzene in which the dihydroperoxide is only slightly soluble. Repeated washing and filtration steps are both time consuming and require expenditure of rather large amounts of hydrocarbon from which the dialkylbenzene and monohydroperoxide must be separated before recycle to the oxidation reaction.

SUMMARY OF THE INVENTION

According to the invention an efficient method of separating para-dialkylbenze dihydroperoxide from para-dialkylbenzene monohydroperoxide and para-dialkylbenzene, comprises suspending the crude oxidation product solids in benzene or other suitable hydrocarbon and heating the mixture to a temperature above a critical temperature of about 60°C. followed by cooling the mixture to a temperature below about 30°C. and recovering the solid product from the mixture. The effectiveness and advantages of this method of product separation and recovery over similar treatments but which do not incorporate both heating and cooling steps is striking as specific comparisons shown hereinafter will illustrate.

DETAILED DESCRIPTION OF THE INVENTION

As noted previously the oxidation reaction mixtures from which crude oxidate solids are recovered are relatively high in dialkylbenzene and monohydroperoxide content. The oxidation reaction comprises oxidation of liquid dialkylbenzene in the presence of a molecular oxygen containing gas and an alkaline material which neutralizes acidic side products. Suitable alkaline materials include alkali and alkaline earth metal oxides, hydroxides, carbonates and bicarbonates, present in amounts of between about 0.1 and about 5% by weight based on the reaction mixture. The oxidation reaction is generally carried out at temperatures between about 90° and about 130° C. under superatmospheric pressure until about 25 to about 50% of the dialkylbenzene has been oxidized calculated as dihydroperoxide. Such a process is well described in the prior art and need only be briefly discussed herein. Amounts of monohydroperoxide in the reaction product mixture are quite large under these reaction conditions and percent completions. For example, at reaction completions of between about 30 and about 40% the ratio of monohydroperoxide to dihydroperoxide in the oxidation reactor effluent is about 3:1. It is the common practice to cool the hot reaction product mixture prior to filtration or other physical separation means in order to recover maximum amounts of dihydroperoxide. For example, the mixture may be placed in a hold tank until it reaches a desired temperature usually below about 40° C. and preferably below about 30° C. Physical separation of the crude oxidate solids from the liquid components may be accomplished by any suitable method such as centrifuging, filtration, etc. From this the initial solid crude oxidate product which is to be treated according to the present invention is obtained. It will be appreciated that although the oxidation reaction mixture or effluent contains a high ratio of monohydroperoxide to dihydroperoxide, for example, in the range of between about 2:1 and about 6:1 respectively, much of the monohydroperoxide will remain in solution in the liquid portion of the mixture or filtrate following separation of crude solids. However, the ratio of monohydroperoxide : dihydroperoxide present in the crude solid oxidate is still undesirably high, being in the range of for example, between about 0.9:1.0 and 0.4:1.0. It should also be understood that the crude solids although in the form of a cake is not composed of all solid product materials but is wet with adsorbed or entrained dialkylbenzene, monohydroperoxide, and water, the latter being present where an aqueous alkaline composition is used in the oxidation reaction and the effluent has not been treated for complete water removal.

The hydrocarbon used to treat the solid dihydroperoxide is preferably an aromatic hydrocarbon selected from benzene, toluene or xylene. The hydrocarbon may also be a dialkylbenzene such as the precursor which is to be oxidized to form the dihydroperoxide, i.e., diisopropylbenzene. An advantage in using a dialkylbenzene is that following separation from the dihydroperoxide, it may be directly recycled together with the monohydroperoxide to the oxidation reactor. On the other hand, some of the precursor will also remain with the filtered oxidate solids. The hydrocarbon selected must be one in which the dihydroperoxide is essentially insoluble at temperatures below about 30° C. and in which the monohydroperoxide is essentially soluble at such temperatures. Benzene has been found to be an outstanding hydrocarbon for the purpose described herein, both because of the relative solubilities of the mono- and dihydroperoxides and its resistance to oxidation if some should be, inadvertantly, recycled to the oxidation reactor.

The temperature to which the hydrocarbon-oxidate solids mixture must be heated is critical. Normally the maximum limit of heating of the mixture is that at which the hydrocarbon would begin to boil and accordingly, in the case of benzene heating temperatures should not exceed about 80° C. at atmospheric pressure. Preferred temperature ranges are between about 60° and about 75° C. for maximum effectiveness. Although lower temperatures may also be contemplated, it should be appreciated that concomitantly lower separation efficiencies will be encountered. However, the hydrocarbon-solid oxidate mixture must be heated to above about 55° C. in order to realize the advantages of the invention disclosed herein. Alternatively, the hydrocarbon itself may be heated and, while hot, added to the cake to achieve a mixture of the required temperature. If the crude oxidate cake also contains significant amounts of moisture, it may be removed by heating the hydrocarbon-crude oxidate mixture sufficiently to distill the hydrocarbon-water azeotrope. The benzene-water azeotrope boiling temperature is slightly above 69° C. at atmospheric pressure. Where other aromatic hydrocarbons are used, such a xylene or toluene, higher azeotropic boiling temperatures will be required unless vacuum distillation conditions are used. The hydrocarbon may also be recovered from the distilled azeotrope by condensing the vapors and separating the hydrocarbon-water phases. It is also desirable to return the separated hydrocarbon to the oxidate mixture thereby avoiding increased concentrations of monohydroperoxide and dialkylbenzene within the mixture.

The amount of hydrocarbon utilized to treat the oxidate solids, generally in the form of a filter cake, may be varied within rather wide limits, for example, between 0.5 and about five times the weight of the crude cake. Especially desirable amounts of hydrocarbon are between about one and about three times that of the filter cake weight. The resulting hydrocarbon-solids mixture, which may be described as a slurry, is agitated or otherwise mixed by any suitable method in order to insure adequate contact of the solid dihydroperoxide particles with the hydrocarbon. Thus, agitation of the mixture aids in separation of monohydroperoxide as well as dialkylbenzene which may be adsorbed on the dihydroperoxide particles.

The second essential step of the treatment according to the invention comprises cooling the hydrocarbon-crude oxidate solids mixture to at least below about 35° C. and preferably to temperatures below about 30° C. Although lower temperatures may also be utilized, they usually require the use of additional cooling means. Effective cooling may be accomplished by merely allowing the hydrocarbon-dihydroperoxide mixture to stand until sufficiently cooled. It is only after the cooling step that the mixture is filtered to separate solid dihydroperoxide.

It has been found that by following the above-described treatment of a crude oxidate cake containing both mono- and dihydroperoxide as well as dialkylbenzene recovery of dihydroperoxide is extremely effective as compared to other methods. For example, the amount of monohydroperoxide present in the solid product recovered by suspending a crude filter cake in hydrocarbon, heating, cooling and refiltering is reduced to about ⅛–1/10 that amount originally present in the crude cake. Such an efficient separation and purification is even further emphasized by empirical data showing that the amount of monohydroperoxide in a cake treated according to the invention is about ⅓ of the amount of monohydroperoxide present in a filter cake recovered after suspension of a crude cake in benzene and filtration at room temperature (about 25° C.) and is at least twice as effective as suspension and filtration at 60° C. The method of the invention also results in dihydroperoxide yields essentially equivalent to yields recovered by direct filtration of an oxidation reaction mixture at 25° C. Yet the inventive process also realizes significantly improved yields over suspension and filtration of a hycrocarbon-solid oxidate mixture at 60° C. in which there is a greater loss of the dihydroperoxide.

It will be appreciated that the benzene or other hydrocarbon recovered as filtrate from the separation of the purified solid dihydroperoxide contains monohydroperoxide as well as dialkylbenzene removed from the crude oxidate cake. Since both are valuable precursors in preparing dihydroperoxide it is desirable to separate and recover these materials for recycle to the oxidation reactor. Although such a separation does not form a part of the present invention it will be understood that effective separation may be accomplished by separating the benzene from the dialkylbenzene and monohydroperoxide by any suitable method.

The dihydroperoxide which is separated and recovered by this method contains only small or negligible amounts of monohydroperoxide. As previously explained, undesired water may also be effectively removed by azeotropic distillation. Thus, the method disclosed herein provides a valuable process for separating materials from the desired dihydroperoxide and is especially useful in a process where efficiency, high product yields and purity are of utmost importance.

The following examples illustrate the manner in which the invention is carried out. It is to be understood that the examples are for the purpose of illustration only and are not to be considered as limiting in any way the materials or conditions disclosed therein. Although the specific para-dialkylbenzene treated is para-diisopropylbenzene, other reactants such as paradi-sec-butylbenzene may also be similarly used to recover the corresponding dihydroperoxide.

EXAMPLE I

An oxidation reactor effluent prepared by reacting paradiisopropylbenzene in the presence of a 10% aqueous solution of sodium carbonate and an oxygen-nitrogen gaseous mixture at a temperature of about 110° C. was treated to remove water. The reaction mixture contained a ratio of para-diisopropylbenzene monohydroperoxide : para-diisopropylbenzene dihydroperoxide of about 2.4:1.0 respectively. The mixture was cooled to about 25° C. and filtered through a coarse fritted glass filter. Filtration was continued for about 15 minutes after the liquid level disappeared into the surface of the filter cake. The crude oxidate solids were analyzed and found to conatin a mole ratio of monohydroperoxide : dihydroperoxide of 0.52:1.0 and a dihydroperoxide recovery of 79.9%. The crude cake was suspended in 2 parts by weight hot benzene with the temperature of the resulting slurried mixture maintained at about 60° C. The mixture was thoroughly admixed by stirring for about 15 minutes to insure sufficient contact of the benzene with solid dihydroperoxide particles and thereafter cooled to about 24° C. The mixture was filtered as previously described and the solids recovered and analyzed for para-diisopropylbenzene dihydroperoxide and para-diisopropylbenzene monohydroperoxide. It was found that the mole ratio of monohydroperoxide to dihydroperoxide was 0.05:1.0. Further analysis of the product showed dihydroperoxide recovery of 74.7% by weight of that present in the oxidation reactor effluent.

EXAMPLE II

By comparison the method carried out as set forth in Example I was repeated with the exception that the crude filter cake was suspended in benzene at about 24° C., mixed for about 15 minutes and thereafter filtered at the same temperature. The mole ratio of monohydroperoxide to dihydroperoxide was found to be 0.16:1.0 with a dihydroperoxide recovery of 75.4%.

EXAMPLE III

The method set forth in Example I was again repeated with the exception that the slurried benzene-crude oxidate mixture maintained at 60° C. was filtered without further cooling. The mole ratio of monohydroperoxide to dihydroperoxide recovered in the filter cake was found to be 0.12:1.0 with a dihydroperoxide recovery of 66.0%.

As is clearly evident from the above Examples the recovery of the dihydroperoxide as shown in Example I yields significantly improved results over similar methods in which either heating or cooling steps were omitted. The method of the invention offers significant advantages over continued washing of a filter cake with benzene or other hydrocarbons at either ambient or elevated temperatures which would otherwise result in undue losses of the desired hydroperoxide product. These as well as other advantages will be evident to those skilled in the art.

What is claimed is:

1. In the recovery of para-diisopropylbenzene dihydroperoxide from an oxidation reactor effluent containing dihydroperoxide and the corresponding monohydroperoxide by physically separating crude solid oxidate from the effluent, the improvement comprising mixing the solid oxidate with an aromatic hydrocarbon in which the monohydroperoxide is soluble and dihydroperoxide is essentially insoluble at temperatures befow about 30°C, said hydrocarbon being selected from the class consisting of benzene, toluene, xylene, and para-dialkylbenzenes, in a weight ratio of between about 2:1 and 1:5 respectively, maintaining the resulting mixture at a temperature of between about 55°C and the boiling point of said hydrocarbon with sufficient agitation to form a slurry, cooling the slurried mixture to a temperature below about 30°C and recovering the dihydroperoxide.

2. An improved method of treating crude oxidate solids comprising para-dialkylbenzene dihydroperoxide, para-dialkylbenzene monohydroperoxide, para-dialkylbenzene and water, which method comprises the steps:

a. adding an aromatic hydrocarbon to the solids which will form an azeotrope with water in an amount of between about 0.5 and about 5 times the weight of solids to form a mixture, said aromatic hydrocarbon being one in which the monohydroperoxide is soluble and dihydroperoxide is essentially insoluble at temperatures below about 30°C and selected from the class consisting of benzene, toluene, xylene, and para-dialkylbenzenes, b. heating the mixture to a temperature of at least about 55°C and sufficient to distill water-hydrocarbon azeotrope, c. cooling the mixture to below about 30°C, and d. physically separating solid dihydroperoxide.

* * * * *

UNITED STATES PATENT OFFICE

CERTIFICATE OF CORRECTION

Patent No. 4,001,338 Dated January 4, 1977

Inventor(s) Ward J. Burkholder

It is certified that error appears in the above-identified patent and that said Letters Patent are hereby corrected as shown below:

In Column 1, line 15, delete the word "percursors" and insert therefor --precursors--.

In Column 6, line 26, delete the word "befow" and insert therefor --below--.

Signed and Sealed this

Thirty-first Day of May 1977

[SEAL]

Attest:

RUTH C. MASON
*Attesting Officer*

C. MARSHALL DANN
*Commissioner of Patents and Trademarks*